Figure 1:
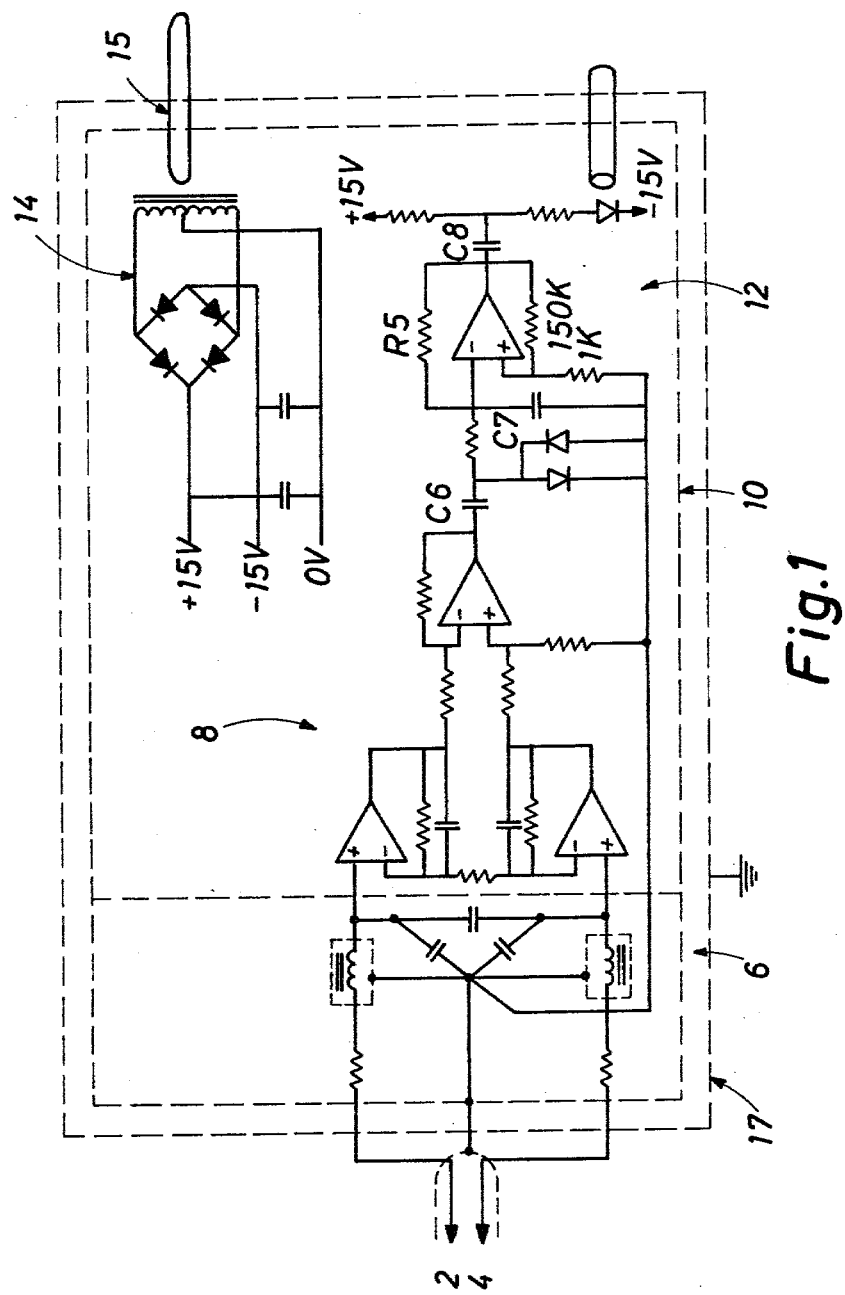
Figure 2:
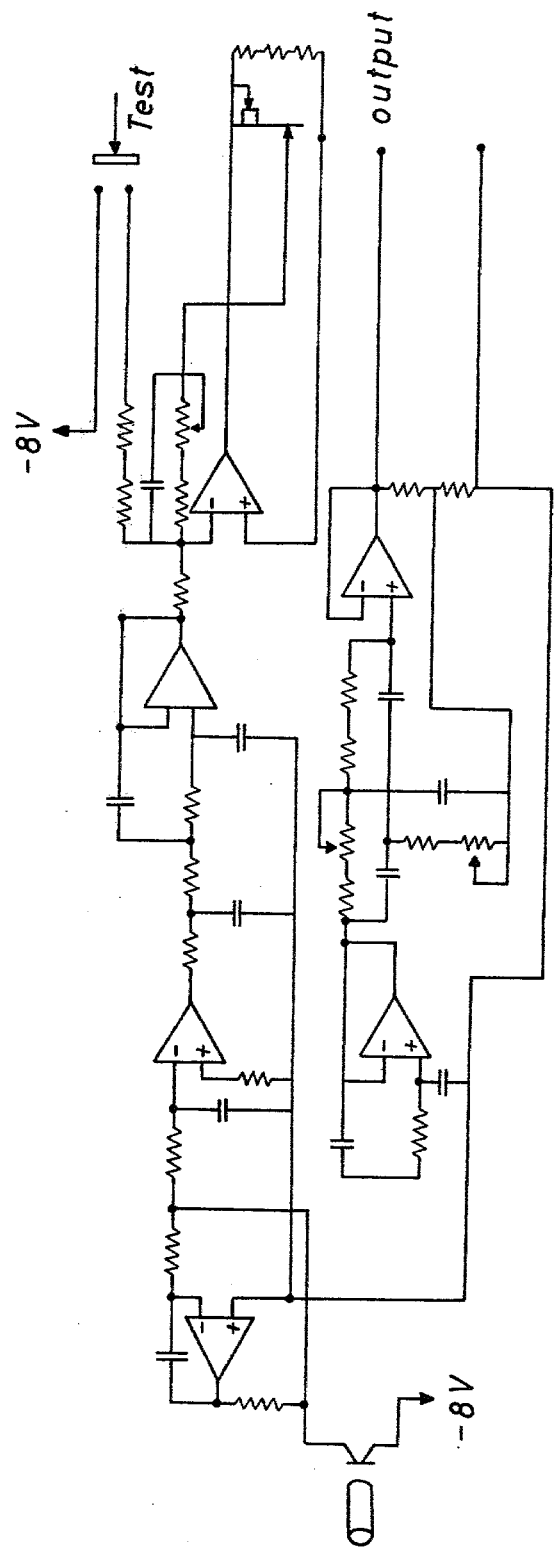

United States Patent [19]

Schmidt-Andersen

[11] 4,245,649
[45] Jan. 20, 1981

[54] DEVICE FOR MONITORING BIOLOGICAL SIGNALS FROM PATIENTS, WHILE AN ELECTRO-SURGICAL APPLIANCE IS BEING SIMULTANEOUSLY USED

[76] Inventor: Poul Schmidt-Andersen, Løvtoften 31, DK-2630 Tåstrup, Denmark

[21] Appl. No.: 927,838

[22] Filed: Jul. 25, 1978

[51] Int. Cl.³ .................................... A61B 17/36
[52] U.S. Cl. .................. 128/696; 128/804; 128/303.17
[58] Field of Search ........... 128/639, 699, 804, 901, 128/908, 696, 303.13, 303.17

[56] References Cited

U.S. PATENT DOCUMENTS

| | | | |
|---|---|---|---|
| 3,500,823 | 3/1970 | Richardson et al. | 128/639 |
| 3,620,208 | 11/1971 | Higley et al. | 128/639 X |
| 3,915,154 | 10/1975 | Cosentino | 128/696 |
| 3,960,141 | 6/1976 | Bolduc | 128/303.13 X |
| 3,968,802 | 7/1976 | Ballis | 128/908 X |
| 4,106,494 | 8/1978 | McEachern | 128/696 |

*Primary Examiner*—Kyle L. Howell
*Attorney, Agent, or Firm*—John T. Synnestvedt; Kenneth P. Synnestvedt

[57] ABSTRACT

The present invention relates to a system for use in monitoring a biological signal from a patient while an electro-surgical appliance which applies a high r.f. voltage, is being simultaneously used. The signals from a number of transducers are transmitted to an amplifier preferably an ECG amplifier with an input-filter. The amplifier is situated in a Faraday cage which is connected to one of the transducers. The filter is a screened HF-filter and the filter together with the Faraday cage is enclosed in an earth connected grounded container or screen. As a result radiation from the Faraday cage is substantially eliminated.

3 Claims, 1 Drawing Figure

DEVICE FOR MONITORING BIOLOGICAL SIGNALS FROM PATIENTS, WHILE AN ELECTRO-SURGICAL APPLIANCE IS BEING SIMULTANEOUSLY USED

The invention relates to a device for use in monitoring a biological signal from a patient while an electro-surgical appliance which applies a high r.f. voltage is being simultaneously used.

An ECG device is known from U.S. Pat. No. 3,915,154. The screen or shield of the cable connected to the ECG electrodes is linked to a screen surrounding the ECG amplifier. This device is suitable for suppressing noise voltages emanating from the mains. However, ECG signals are not detected in this device in the case where an r.f. signal having a magnitude of several hundred volts is fed to the tissue.

Even if an r.f. filter is interposed before the ECG amplifier, it will nevertheless be impossible to detect the ECG signals reliably enough. In fact radiation outside and inside the screen will affect the operation of the device.

According to the present invention, there is provided a device which monitors a biological function of a patient during use of an electro-surgical appliance which delivers high r.f. voltages to the tissue under consideration, comprising at least one sensor which, when linked to the patient, provides a signal representative of the biological function, which signal is supplied via a screened r.f. filter to an amplifier, the filter and amplifier being disposed within a Faraday cage which is connected to a reference potential and insulated from a surrounding earthed or grounded container. Thus, in a device according to the invention, the radiation emanating from the filter inductors is screened, and so is radiation emanating from the Faraday cage.

It is advantageous for the inductors of the filter at the input of the amplifier to be separately screened.

Preferably the device is so arranged that the capacity between the Faraday cage and the external screening container, which is earthed when the device is in use, is in the range 30 to 60 pF. As a result the r.f. signal is to some extent short-circuited, but the inflowing r.f. currents are not so large that the r.f. voltage drop in the tissue of the patient becomes excessive.

Where the transducer means requires a voltage feed, as opposed to ECG electrodes which require no applied voltage, this voltage feed may be applied via a further filter or filters whose inductors are fitted and screened in the screened Faraday cage, in which case the power supply used may be the power supply which is used for energizing the amplifier.

A specific embodiment of a device according to the present invention will now be described by way of example with reference to the accompanying drawing wherein:

FIG. 1 is a circuit diagram of circuitry, including an ECG amplifier, fitted in a screened Faraday cage.

One form of electro-surgical appliance, with which a device according to the present invention can be used, comprises a radio-frequency source of which one electrode having a relatively large surface area is arranged to be coupled to the back of a patient, and of which the other electrode consists for example of the knife used by the surgeon. During an operation, bleeding is stopped by sending r.f. currents amplitude-modulated at 50 Hz through the tissue under the control of the surgeon by use of a pedal-operated control device. In the first place, coagulation occurs, in the second place there is a certain amount of carbonisation, and in the third place the tissue dries out. All these things contribute to stopping the bleeding. The applied voltage is preferably in the range 300–400. The frequency is preferably in the range 750 kHz–1.6 MHz; such a frequency does not upset the nerve-cells of the tissue.

The device illustrated in this embodiment comprises electrodes or transducer means which, for ECG monitoring, may be one reference electrode and two ECG electrodes. The reference electrode is connected to a metal container 10 which acts as a Faraday cage. The two active electrodes are connected to the input terminals 2,4 of a symmetrically constructed filter 6, which provides an attenuation of about 70 dB at 1 MHz. The filter has inductors L1 and L2 which are individually screened as indicated in FIG. 1. The output of the filter is connected to an ECG amplifier 8 (the attenuation by 70 dB prevents the amplifier from being overloaded by the modulation signal of the r.f. signal), which is fitted in a part 11 of the Faraday cage 10, the whole of which is enclosed in and insulated from a screening container 17. The capacity between the cage 10 and the screening container 17 is in the range 30–60 pF. This arrangement results in the r.f. signal being to some extent short-circuited, thus limiting the change in potential of the cage 10. The ECG amplifier 8 is of the fully symmetrical type, with a gain of about 40 times over a frequency range extending to below one Hz. The amplifier comprises matched resistances, thus avoiding any resistance adjustment. Following the ECG amplifier 8 is an attenuator including two diodes parallel D1, D2 coupled in opposition, which has the effect, should overloading occur, of clamping the signal level. The output signal of the ECG amplifier 8 (of about 41 mV) is fed via a capacitor C6 to a self-oscillating multivibrator 12.

When the device is energized, the multivibrator acts in the following manner:

Feedback to the positive terminal—see FIG. 1—sets up an initial voltage of about 66 mV (10 V 150) at the positive input. The capacitor C7, which has zero volts across it at the moment when the device is switched on, is charged up via the feedback resistor R5. After a certain time, the capacitor C7 reaches 66 mV, and then the output changes abruptly from its positive level to its negative level. The potential of the positive input is then at −66 mV, with the result that the capacitor C7 then charges towards −10 V until the voltage of −66 mV is reached and the cycle then repeats continuously. The frequency of oscillation is about 1 kHz.

As mentioned, the output signal of about 41 mV of the ECG amplifier is fed to the input of the multivibrator 12. This is to modulate the charging of the capacitor C7 and thereby modulate the pulse-width of the multivibrator 12. This modulation depends unambiguously on the ECG signals. A coupling capacitor C8, having a value of 2.2 nF, differentiates the output signal of the multivibrator (rectangular-wave signal) and passes only the flanks to a light-emitting diode D3. As a result, only a brief glimmer of light occurs at each change of state of the multivibrator 12. This manner of modulation saves enegy.

Figure 3:
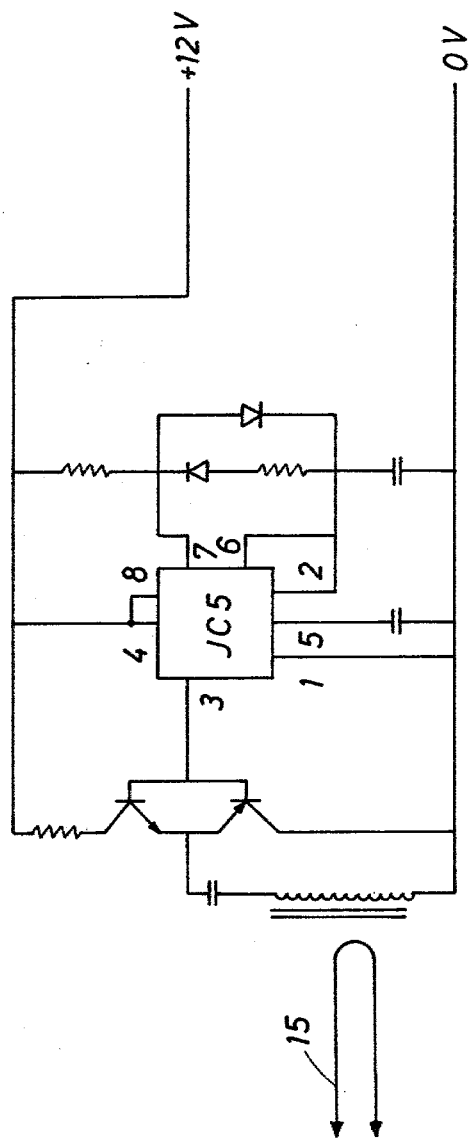

A d.c. voltage supply arrangement 14 for the ECG amplifier comprises a rectifier bridge fitted in the cage 10. To the rectifier bridge is connected a toroidal winding which is connected via a single turn 15 to a toroidal winding of an inverter, shown in FIG. 3, disposed outside the cage 10. The capacity between the toroidal windings is about 0.7 pF and the capacity of each toroidal winding is about 1.4 pF.

The light-emitting diode D3 transmits light to a phototransistor of the demodulator via a light pipe LP, and the capacitance between diode D3 and the phototransistor can be as small as desired by appropriately selecting the distance between them.

An additional advantage is that the transmission path of the power supply is different from the transmission path of the output signal. This prevents any cross-modulation which might otherwise occur. It is also an advantage that the capacity is at its lowest in the transmission path of the output signal.

The amplitude of the r.f. signal may be optionally reduced by appropriately positioning the ECG electrode. Since the patient is always receiving and transmitting a signal at 50 Hz, the positioning of the electrodes may be checked with this signal. By measuring the strength of the 50 Hz signal received at the electrodes, it can be determined whether or not the skin under the electrodes must be further abraded (the d.c. or low frequency resistance must be below 5 kΩ), and whether they must be fitted such that they are on a line at right-angles to the r.f. current. When the electrodes are properly fitted, a filter which filters off the remainder of the 50 Hz signal is coupled into the output stage (the demodulator).

Whereas the above described device has been described in connection with monitoring of ECG signals, it will be appreciated that it can be readily modified as appropriate for monitoring other biological signals, for example those representing blood pressure and temperature, EEG and EMG. In the case of monitoring blood pressure and temperature signal, the voltage on the secondary side of the transformer in the Faraday cage is reduced, and the voltage is fed out to the transducers via a filter (which is likewise fitted in the cage and has individually screened inductors).

I claim:

1. A device for monitoring a biological function of a patient during use of an electro-surgical appliance which delivers high r.f. voltages to the tissue under consideration, the device comprising a reference electrode and two active electrodes adapted to contact the body of the patient, thereby providing a signal representative of the biological function, a signal amplifier having two input terminals, a shielded conductor and a filter for connecting the electrodes with the amplifier, the reference electrode, and the conductor shield being interconnected, and each of the active electrodes, being connected to an amplifier input terminal, an ungrounded shield surrounding said filter and said amplifier, and a grounded container surrounding and insulated from the ungrounded shield.

2. A device as claimed in claim 1, wherein the filter incorporates an inductor and in which the inductor is provided with an individual shield.

3. A device as claimed in claim 1, characterized in that the r.f. voltage has a frequency in the range from 750 kHz to 1.6 MHz and in which the capacitance between the ungrounded shield and the grounded container is in the range of 30 to 60 pF.

* * * * *